United States Patent [19]

Campbell et al.

[11] Patent Number: 4,855,471

[45] Date of Patent: Aug. 8, 1989

[54] PROCESS FOR THE CHLORODEPHENYLATION OF PHENYLDISILANES

[75] Inventors: William H. Campbell; Terrence K. Hilty, both of Midland, Mich.

[73] Assignee: Dow Corning Corporation, Midland, Mich.

[21] Appl. No.: 146,065

[22] Filed: Jan. 20, 1988

[51] Int. Cl.[4] ........................ C07F 7/08

[52] U.S. Cl. ........................ 556/430

[58] Field of Search ........................ 556/430

[56] References Cited

U.S. PATENT DOCUMENTS

| | | | |
|---|---|---|---|
| 4,291,167 | 9/1981 | Allain et al. | 556/430 |
| 4,707,557 | 11/1987 | Nagai et al. | 556/430 |
| 4,716,240 | 12/1987 | Nagai et al. | 556/430 |

OTHER PUBLICATIONS

Nagai et al., *Org. Pre. Proc. Intel.,* 13, pp. 118 (1981).

Matsumoto, *J. Synth. Org. Chem. Japan,* 40, pp. 490–500.

Ziegler et al., *Polymer Preprints,* 28(1), pp. 424–425 (1987).

Bettler et al., *Inorganic Chemistry,* 9(5), pp. 1060–1065 (1970).

Kumada et al., *J. Organometallic Chem.,* 2, pp. 478–484 (1964).

Kumada et al., *J. Organometallic Chem.,* 43(2), pp. 293–305 (1972).

Ishikawa et al., *J. Organometallic Chem.,* 118(2), pp. 139–153 (1976).

Hengge et al., *Monatsh. Chem.,* 106(4), pp. 887–892 (1975).

Gilman et al., *Chemistry and Industry,* Nov. 8, 1958, pp. 1479–1480.

*Primary Examiner*—Paul F. Shaver

*Attorney, Agent, or Firm*—Carl A. Yorimoto

[57] ABSTRACT

A process for the chlorodephenylation of a phenyl-containing disilane to produce alkylhalodisilanes is described. The process comprises (A) adding an aluminum halide, $AlX_3$, to a phenyl-containing disilane, having the formula, $$R_{3-a}(C_6H_5)_aSiSiR_{3-b}(C_6H_5)_b,$$

wherein the phenyl-containing disilane has a melting point lower than about 50° C.; and the aluminum halide is added to a concentration greater than about 1 mole percent relative to the phenyl-containing disilane; (B) contacting the phenyl-containing disilane and the aluminum halide, in the absence of a solvent, with excess anhydrous hydrogen halide gas at a temperature less than about 50° C.; (C) facilitating conversion of the phenyl-containing disilane to the alkylhalodisilane; and (D) isolating and recovering the alkylhalodisilane.

11 Claims, No Drawings

PROCESS FOR THE CHLORODEPHENYLATION OF PHENYLDISILANES

BACKGROUND OF THE INVENTION

The instant invention relates to the preparation of alkylhalodisilanes from phenyl-containing disilanes. More specifically, the instant invention relates to the preparation of alkylhalodisilanes having the formula, $$R_{3-a}X_aSiSiR_{3-b}X_b,$$

wherein each R is an independently selected alkyl group; X is a halogen atom; a has a value of 0, 1, 2, or 3; and b has a value of 1, 2, or 3.

Alkylhalodisilanes have value as chemical intermediates. Nagai et al., *Org Pre. Proc. Intl.,* 13. pg 118 (1981), discloses the synthesis of p-bis(hydroxydimethylsilyl)-benzene starting with the reaction of 1,2-dichloro-1,1,2,2- tetramethyldisilane and p-dibromobenzene. Matsumoto, *J. Synth. Org. Chem. Japan,* 40, pp. 490–500 (1982), discloses the preparation of allylmethyldichlorosilane from the reaction of 1,1,2,2-tetrachloro-1,2-dimethyldisilane with allyl chloride.

The alkylhalodisilane, $(CH_3)_3SiSiCH_3Cl_2$, has been shown to be a useful monomer in the preparation of polysilane polymers. Ziegler et al., *Polymer Preprints,* 28 (1). pp. 424–425 (1987), shows that polysilane polymers prepared from this monomer have unique photochemical properties.

Methylchlorodisilanes are a by-product of the preparation of methylchlorosilanes via the direct process reaction of methyl chloride with silicon. The by-product methylchlorodisilanes will be a mixture of all possible combinations methyl-containing and chlorine-containing disilanes. Extensive distillation would be necessary to isolate the desired disilane species.

Bettler et al., *Inorganic Chemistry,* 9(5), pp. 1060–1065 (1970), discloses the preparation of 1,1,1,2-tetramethyldichlorodisilane via the reaction of bis(trimethylsilyl)mercury with methyldichlorosilane. Hexamethyldisilane was a by-product of this reaction.

Kumada, Ishikawa, and Maeda, *J. Organometallic Chem.,* 2, pp. 478–484 (1964), disclose that certain alkylhalotrisilanes and alkylhalotetrasilanes can be prepared from the corresponding phenyl-substituted alkylpolysilanes by reaction with hydrogen chloride in chloroform solvent in the presence of anhydrous aluminum chloride. However, Kumada et al. discloses that this chlorodephenylation reaction is only applicable to phenyl-substituted methylchloropolysilane where a silicon atom is attached to only one phenyl grup. In the examples of Kumada et al., reaction times of about 16 hours and moderate yields ranging from 53 to 76 percent are disclosed.

Kumada et al. *J. Organometallic Chem.,* 43(2); pp. 293–305 (1972), discloses two methods for preparing 1,1-dichlorotetramethyldisilane from 1,1-diphenyltetramethyldisilane. In the first method, 1,1-diphenyltetramethyldisilane was added to cold concentrated sulfuric acid. Ammonium chloride was then added to the acid mixture. The resulting organic layer was separated and distilled. A yield of 61 percent 1,1-dichlorotetramethyldisilane resulted.

In the second method disclosed by Kumada et al. aluminum chloride was added to a benzene solution of 1,1-diphenyltetramethyldisilane. Dry hydrogen chloride was passed through the solution. The resulting mixture was distilled. A yield of 69 percent 1,1-dichlorotetramethyldisilane resulted.

Ishikawa et al., *J. Organometallic Chem.,* 118(2), pp. 139–153 (1976), discloses a similar preparation of 1,1-dichlorotetramethyldisilane as reported by Kumada et al. in which anhydrous aluminum chloride is added to a benzene solution of 1,1-diphenyltetramethyldisilane, this mixture then being contacted with dry hydrogen chloride. The result was a 59 percent yield of 1,1-dichlorotetramethyldisilane.

Hengge et al., *Monatsh. Chem.,* 106(4); pp. 887–892 (1975), discloses the preparation of several methylhalodisilanes from phenyl-containing disilanes. One of the materials disclosed was the preparation of 1,1-dichloro-1,2,2,2-tetramethyldisilane from 1,1,1,2-tetramethyl-2,2-diphenyldisilane. The 1,1,1,2-tetramethyl-2,2-diphenyldisilane was placed in a sealed tube with excess hydrogen chloride gas. The contents of the sealed tube were held for 5 days. The liquid was then distilled to give a 94 percent yield of 1,1-dichloro-1,2,2,2-tetramethyldisilane. Hengge et al. does not mention the use of any catalyst to facilitate the reaction.

SUMMARY OF THE INVENTION

The objective of the instant invention is to provide a process for the preparation of alkylhalodisilanes in a form essentially pure to facilitate ease of isolation and recovery of the desired alkylhalodisilane. A further objective is the preparation of the desired alkylhalodisilane in a process that requires a minimum of process time. Reaction of phenyl-containing disilanes with anhydrous hydrogen chloride in the presence of an effective amount of a Lewis acid catalyst in the absence of a solvent to remove the phenyl groups as benzene and to insert corresponding chlorine atoms accomplishes these objectives.

The inventors have found that Lewis acid materials such as metal halides, as examples, aluminum halides, ferric halides, and zinc halides are catalysts for the chlorodephenylation reaction to convert phenyl-containing disilanes to alkylhalodisilanes. However, aluminum halides are the preferred catalyst because they provide faster reaction which corresponds to minimum process time. The inventors believe that limited solubility of other Lewis acid materials limits the effectiveness of these materials as catalysts for the instant invention. Aluminum chloride, as an example, facilitates the chlorodephenylation reaction to essentially completely convert a phenyl-containing disilane to an alkylhalodisilane in a matter of minutes and hours rather than days.

DESCRIPTION OF THE INVENTION

In accordance with the instant invention a process for the preparation of alkylhalodisilanes from phenyl-containing disilanes is provided under conditions that will be described herein. What is described, therefore, is a process for the preparation of an alkylhalodisilane having the formula, $$R_{3-a}X_aSiSiR_{3-b}X_b,$$

wherein each R is an independently selected alkyl group; X is selected from a group consisting of chlorine and bromine atoms: a has a value of 0, 1, 2 or 3; and b has a value of 1, 2, or 3, said process comprising (A) adding an aluminum halide, $AlX_3$, to a phenyl-containing disilane, having the formula, $$R_{3-a}(C_6H_5)_a SiSiR_{3-b}(C_6H_5)_b,$$

wherein R, a, b, and X are defined above, wherein the phenyl-containing disilane has a melting point lower than about 50° C.; and the aluminum halide is added to a concentration of about 1 mole percent or greater relative to the phenyl-containing disilane;

(B) contacting the phenyl-containing disilane and the aluminum halide. in the absence of a solvent, with excess anhydrous hydrogen halide gas at a temperature less than about 50° C.;

(C) facilitating conversion of the phenyl-containing disilane to the alkylhalodisilane; and (D) isolating and recovering the alkylhalodisilane.

The chlorodephenylation reaction to convert phenyl-containing disilanes to alkylhalodisilanes can be represented by the following:

$$R_{3-a}(C_6H_5)_a SiSiR_{3-b}(C_6H_5)_b + \text{Excess HX} \xrightarrow{AlX_3}$$
$$R_{3-a}X_a SiSiR_{3-b}X_b + (a+b)C_6H_6.$$

The instant invention utilizes an aluminum halide as a catalyst to facilitate conversion of the phenyl-containing disilanes to alkylhalodisilanes. It is preferred to conduct the chlorodephenylation reaction in a manner such that the conversion of phenyl-containing disilanes to alkylhalodisilanes is essentially complete. For the purposes of the instant invention. the term "essentially complete conversion" means greater than about 90 percent conversion of the phenyl-containing disilane to the desired alkylhalosilane. The reaction is conducted in the liquid phase without the presence of a solvent. As detailed, infra, a maximum temperature of 50° C. is preferred. Therefore, the reactant phenyl-containing disilane and the desired alkylhalodisilane must have melting points less than about 50° C.

The alkylhalodisilane which is prepared by the instant invention is a material that has a melting point below about 50° C. The alkyl group or groups of the alkylhalodisilane may be any alkyl group containing from 1 to as many as 10 carbon atoms, provided that the alkylhalodisilane has a melting point below about 50° C. It is preferred that the alkyl group or groups have 1 to 4 carbon atoms. The alkylhalodisilanes can be, for example, 1,1-dichloro-1,2,2,2-tetramethyldisilane. 1,1-dichloro-1,2,2,2-tetraethylsilane. 1,1-dichloro-1,2,2,2-tetrabutyldisilane, 1,1-dibromo-1,2,2,2-tetramethyldisilane. 1,2-dichloro-1,1,2,2-tetramethyldisilane, 1,2,-dichloro-1,2,-diethyl-1,2,-di(n-propyl)disilane. or 1-chloro-1,1,2,2,-pentamethyldisilane.

The phenyl-containing disilane which is chlorodephenylated with anhydrous hydrogen chloride (HCl) to produce the desired alkylhalodisilane must also have a melting point lower than about 50° C. and can be, for example. 1,1-diphenyl-1,2,2,2-tetramethyldisilane, 1,1-diphenyl-1,2,2,2-tetraethylsilane, 1,1-diphenyl-1,2,2,2-tetrabutyldisilane, 1,2-diphenyl-1,1,2,2-tetramethyldisilane, 1,2,-diphenyl-1,2,-diethyl- 1,2,-di(n-propyl)disilane, or 1-phenyl-1,1,2,2,2,-pentamethyldisilane.

The hydrogen halide can be for example, hydrogen chloride, or hydrogen bromide. Hydrogen chloride is the preferred hydrogen halide. For the purposes of the instant invention, the term "excess anhydrous hydrogen halide gas" means an excess over the stoichiometric amount of hydrogen halide to effect the chlorodephenylation reaction.

The aluminum halide can be, for example, aluminum chloride, or aluminum bromide. The aluminum halide should correspond to the hydrogen halide which is being applied to produce the desired alkylhalodisilane. Aluminum chloride is the preferred aluminum halide. The aluminum halide can be utilized in such forms as powders, granules, or other forms which are readily dissolved to insure ready reactivity with the reactant phenyl-containing disilane and the hydrogen halide.

To effect chlorodephenylation of a phenyl-containing disilane, the aluminum halide should be added to the reaction mixture to a concentration of about 1 mole percent or greater relative to the starting phenyl-containing disilane. More preferably, the aluminum halide should be added to a concentration in a range from about 1 to 10 mole percent relative to the starting phenyl-containing disilane. This level of aluminum halide is sufficient, under the conditions of the instant invention, to effect the chlorodephenylation reaction in less than about 8 hours. Aluminum halide concentrations above 10 mole percent may be utilized; however, increased cleavage of organic groups and rearrangement of substituent groups bonded to silicon atoms may occur.

The instant invention is preferably carried out in the absence of a solvent. It has been found that solvents have an inhibiting effect upon the essentially complete conversion of phenyl-containing disilanes to the desired alkylhalodisilanes. However, small amounts of solvent, incidental to the conduct of the process, are not believed to be detrimental to the instant invention.

The phenyl-containing disilane is contacted with excess hydrogen halide gas in the presence of an aluminum halide catalyst at a temperature less than about 50° C. Temperatures greater than about 50° C. can lead to cleavage of organic groups and rearrangement of substituent groups bonded to silicon atoms.

To facilitate the reaction of the phenyl-containing disilane with hydrogen halide, the reaction mixture should be maintained in the liquid phase. Based upon the temperature limitation of a maximum of about 50° C., the phenyl-containing disilane and the desired alkylhalosilane should both have a melting point less than about 50° C. More preferably, the melting point of the reaction mixture should be less than about 40° C.

The chlorodephenylation of a phenyl-containing disilane can be carried out in conventional means of contacting gases, liquids, and solids. These means can be such process configurations as a stirred reactor operating at atmospheric pressure in which an excess of hydrogen halide gas is passed through a mixture of the phenyl-containing disilane and the aluminum halide catalyst. The excess hydrogen halide gas is vented. A modification of this previous configuration is a process in which the pressure of the contact vessel is maintained at a pressure above atmospheric pressure, the venting of excess hydrogen halide gas being controlled to maintain the desired pressure. Further, the process configuration can be one in which excess hydrogen halide is added as a liquified gas and which the reactor is a closed system which will operate at the autogenous pressure of the hydrogen halide. The contact vessel should be provided with means for cooling to remove the heat generated by the exothermic reaction to maintain the desired temperature of less than about 50° C.

The vessel in which the phenyl-containing disilane and the hydrogen halide are contacted can be operated at a pressure greater than about atmospheric pressure.

An advantage of operation at pressure is the increased solubility of the hydrogen halide in the disilane mixture.

Isolation and recovery of the desired alkylhalodisilane can be effected by such known means as distillation. Distillation can isolate the desired alkylhalodisilanes at a yield of greater than about 85 percent at a purity of greater than about 95 percent. For the purposes of the instant invention "yield" means the percent recovery of the theoretical amount of the desired alkylhalodisilane available based upon the amount of the starting phenyl-containing disilane.

So that those skilled in the art may better understand and appreciate the instant invention. the following examples are presented. These examples are presented as illustrative and are not to be construed as limiting the claims of the instant invention.

EXAMPLE 1(Not within the scope of the instant invention)

A run was made in an attempt to react 1,1-diphenyl-1,2,2,2-tetramethyldisilane (DPTMDS) with anhydrous hydrogen chloride (HCl) to form 1,1-dichloro-1,2,2,2-tetramethyldisilane (DCTMDS) without a catalyst.

DPTMDS was prepared by a technique similar to that disclosed by Gilman et al., *Chemistry and Industry*, Nov. 8, 1958, pp. 1479-1480. In this technique. diphenylmethylchlorosilane was added to a mixture of lithium metal and tetrahydrofuran. The resulting lithium adduct was reacted with excess trimethylchlorosilane. The product mixture was filtered from the resultant solids. DPTMDS was recovered by vacuum distillation at a purity of about 97 percent.

Dry HCl gas was bubbled through DPTMDS in a glass flask for a period of about 24 hours at ambient temperature. The excess HCl vented through a water cooled condenser. The contents of the flask were sampled and analyzed by gas chromatography (GC). Identification of individual compounds was previously effected by nuclear magnetic resonance (NMR) and mass spectroscopy. Analyses showed no detectable levels of DCTMDS.

The results demonstrate that under the above conditions the reaction of DPTMDS with excess HCl does not proceed without an effective catalyst.

EXAMPLE 2 (Not within the scope of the instant invention)

DPTMDS (0.05 mole) was placed in a 300 ml capacity closed stainless steel cylinder fitted with a needle valve. The cylinder was connected to a vacuum source and degassed. The cylinder was then cooled in liquid nitrogen and evacuated. Dry HCl (0.23 mole) was condensed into the cylinder. The cylinder was closed, and the contents of the cylinder were held at room temperature for 5 days. At the end of this period, excess HCl and by-product benzene were removed at room temperature and reduced pressure. The liquid product was analyzed by GC. Analyses showed that the product was 90 percent DCTMDS.

The above experiment was repeated twice using similar apparatus and procedures as above. Two different closed cylinders were utilized. In one case, DPTMDS was converted only 50 percent to DCTMDS after 5 days. The product of this reaction was water white. In the second case, DPTMDS was completely converted to DCTMDS in 2 days. The product from the second reaction was yellow in color, the yellow color being indication of a possible soluble iron compound.

The above results suggest that the stainless steel cylinder, its surface or other contaminant catalyzes the reaction of DPTMDS with excess HCl. However, complete conversion of DPTMDS to DCTMDS occurs only after prolonged contact time.

EXAMPLE 3 Using apparatus and procedures similar to those utilized in Example 1, 109.2 g (0.40 mole) DPTMDS and 1.05 g ($7.88 \times 10^{-3}$ mole) aluminum chloride were charged to the glass flask. Dry HCl gas was bubbled through the mixture and the excess was vented through an open condenser. A significant exotherm was noted. After 4.5 hours of constant HCl feed, the mixture was sampled. GC analysis showed that the DPTMDS was converted completely to DCTMDS. The entire mixture was distilled at ambient pressure to yield 74.9 g of a product boiling at 147°-148° C. The product was determined by GC analyses to be essentially 100 percent of the desired DCTMDS. Therefore, conversion of DPTMDS to DCTMDS was essentially 100 percent and product recovery or yield via distillation was 89.5 percent.

The above results demonstrate that aluminum chloride is an effective catalyst at low concentrations for the reaction of DPTMDS with excess HCl to produce DCTMDS.

EXAMPLE 4 Using similar apparatus, smaller in size, and procedures similar to those utilized in Example 3, four runs were made with DPTMDS contacted with varying levels of aluminum chloride. These four runs are designated as Samples AA, BB, CC, and DD, respectively. The progress of each run was monitored by sampling and GC analyses, the time needed to reach complete conversion of DPTMDS to DCTMDS being noted. Table 1 is a summary of these runs. In Table 1 the concentration of aluminum chloride relative to the DPTMDS, expressed in mole percent is denoted as "% $AlCl_3$"; the time required for complete conversion of DPTMDS to DCTMDS, expressed in minutes, is denoted as "Time".

TABLE 1

| Sample | % $AlCl_3$ | Time |
| --- | --- | --- |
| AA | 4.2 | 20 |
| BB | 2.1 | 80 |
| CC | 1.4 | 390 |
| DD | 1.0 | >1320 |

It should be noted that for Sample DD, at 22 hours, the sample taken analyzed approximately 22 percent DCTMDS and 78 percent 1-chloro-1-phenyl-1,2,2,2-tetramethyldisilane.

The above results further demonstrate that aluminum chloride at an appropriate level is an effective catalyst for the reaction of DPTMDS with excess HCl to produce DCTMDS. Additionally, it is demonstrated that complete conversion can be effected in a matter of minutes or hours.

EXAMPLE 5 (Not within the scope of the instant invention)

Using similar apparatus and procedures to those utilized in Example 3, a run was made to determine the effect of a solvent upon the reaction of the instant invention.

DPTMDS, aluminum chloride and chloroform were added to a flask, the aluminum chloride was added at a concentration of about 5 mole percent relative to the DPTMDS. Chloroform was added at a 2/1 volume ratio relative to the DPTMDS.

After 2 hours bubbling excess anhydrous HCl through the mixture, the mixture in the flask was sampled. Analysis showed the disilane mixture consisted of approximately 20 percent DCTMDS.

The above result demonstrates an apparent inhibiting effect of solvent upon the aluminum chloride-catalyzed reaction of DPTMDS with HCl.

EXAMPLE 6 (Not within the scope of the instant invention)

Using similar apparatus and procedures as those used in Example 5, iron chloride was evaluated as a chlorodephenylation catalyst.

$FeCl_3.6H_2O$ was added to DPTMDS at a concentration of about 2 mole percent. After about 6 hours in which excess HCl was bubbled through the DPTMDS mixture, further reaction ceased. An insoluble precipitate had formed. The DPTMDS mixture was analyzed. It was found that DPTMDS was converted only 50 percent to DCTMDS. An additional 2 mole percent $FeCl_3.6H_2O$ was added to the mixture and excess HCl feed was resumed. After reaction for about 24 hours, DPTMDS was completely converted to DCTMDS.

The above results demonstrate that iron chloride will catalyze the reaction of DPTMDS with excess HCl. However, complete conversion requires at least one day.

What is claimed is:

1. A process for the preparation of an alkylhalodisilane having the formula, $$R_{3-a}X_aSiSiR_{3-b}X_b,$$

wherein each R is an independently selected alkyl group; X is selected from a group consisting of chlorine and bromine atoms; a has a value of 0, 1, 2, or 3; and b has a value of 1, 2, or 3, said process comprising (A) adding an aluminum halide. $AlX_3$, to a phenyl-containing disilane, having the formula.

$$R_{3-a}(C_6H_5)_aSiSiR_{3-b}(C_6H_5)_b,$$

wherein R, a, b, and X are defined above, wherein the phenyl-containing disilane has a melting point lower than about 50° C.; and the aluminum halide is added to a concentration of about 1 mole percent or greater relative to the phenyl-containing disilane;

(B) contacting the phenyl-containing disilane and the aluminum halide, in the absence of a solvent, with excess anhydrous hydrogen halide gas at a temperature less than about 50° C.;

(C) facilitating conversion of the phenyl-containing disilane to the alkylhalodisilane; and (D) isolating and recovering the alkylhalodisilane.

2. A process according to claim 1, wherein b has a value of 2 or 3.

3. A process according to claim 1, wherein X is a chlorine atom.

4. A process according to claim 1, wherein the alkylhalodisilane has the formula, $$R_3SiSiR_{3-b}X_b,$$

and the phenyl-containing disilane has the formula, $$R_3SiSiR_{3-b}(C_6H_5)_b.$$

5. A process according to claim 4, wherein X is a chlorine atom.

6. A process according to claim 1, wherein the aluminum halide is added to a concentration in a range from about 1 to 10 mole percent relative to the phenyl-containing disilane.

7. A process according to claim 1, wherein the phenyl-containing disilane, the aluminum halide, and the excess anhydrous hydrogen chloride are in contact for less than about 8 hours.

8. A process according to claim 1, wherein the phenyl-containing disilane, the aluminum halide, and the excess anhydrous hydrogen chloride are contacted at a pressure greater than atmospheric pressure in a closed system.

9. A process according to claim 1, wherein conversion of the phenyl-containing disilane to the alkylhalodisilane is essentially complete; and the alkylhalodisilane is isolated and recovered at a yield of greater than about 85 percent at a purity of greater than about 95 weight percent.

10. A process according to claim 1, wherein isolating and recovering the alkylhalodisilane is effected by distillation.

11. A process according to claim 1, wherein the alkylhalodisilane is 1,1-dichloro-1,2,2,2-tetramethyldisilane; the phenyl-containing disilane is 1,1-diphenyl-1,2,2,2-tetramethyldisilane; the aluminum chloride is added to a concentration in a range from about 1 to 10 mole percent relative to the 1,1-diphenyl-1,2,2,2-tetramethyldisilane; the 1,1-diphenyl-1,2,2,2-tetramethyldisilane, the excess anhydrous hydrogen chloride, and the aluminum chloride are in contact for less than about 8 hours; conversion of the 1,1-diphenyl-1,2,2,2-tetramethyldisilane to 1,1-dichloro-1,2,2,2-tetramethyldisilane is essentially complete; and the 1,1-dichloro-1,2,2,2-tetramethyldisilane is isolated and recovered by distillation at a yield of greater than about 85 percent at a purity of greater than about 95 weight percent.

* * * * *